United States Patent
Vogedes et al.

(10) Patent No.: US 11,644,310 B2
(45) Date of Patent: May 9, 2023

(54) SYSTEMS AND METHODS FOR POSITIONING DURING ATYPICAL ATMOSPHERIC CONDITIONS

(71) Applicant: NextNav, LLC, Sunnyvale, CA (US)

(72) Inventors: Jerome Vogedes, Milwaukee, WI (US); William Alberth, Jr., Prairie Grove, IL (US)

(73) Assignee: NextNav, LLC, Sunnyvale, CA (US)

( * ) Notice: Subject to any disclaimer, the term of this patent is extended or adjusted under 35 U.S.C. 154(b) by 250 days.

(21) Appl. No.: 16/030,596

(22) Filed: Jul. 9, 2018

(65) Prior Publication Data
US 2019/0041205 A1 Feb. 7, 2019

Related U.S. Application Data (60) Provisional application No. 62/540,549, filed on Aug. 2, 2017.

(51) Int. Cl.
*G01C 5/06* (2006.01)
*G01N 33/00* (2006.01)

(52) U.S. Cl.
CPC .............. *G01C 5/06* (2013.01); *G01N 33/004* (2013.01)

(58) Field of Classification Search
CPC ........................................................ G01C 5/06
See application file for complete search history.

(56) References Cited

U.S. PATENT DOCUMENTS

| | | | |
|---|---|---|---|
| 6,862,525 B1 * | 3/2005 | Beason | G01C 21/20 701/454 |
| 7,424,825 B2 | 9/2008 | Saporito | |
| 9,574,877 B2 | 2/2017 | Sasaki | |
| 2006/0106559 A1 | 5/2006 | Lerch | |
| 2009/0286556 A1 * | 11/2009 | Yumoto | G01C 21/20 455/456.6 |
| 2013/0257650 A1 * | 10/2013 | Miyake | G01L 19/086 342/357.31 |
| 2015/0133145 A1 * | 5/2015 | Palanki | G01C 25/00 455/456.1 |
| 2015/0153171 A1 * | 6/2015 | Zhou | G01C 5/06 702/138 |
| 2015/0233713 A1 * | 8/2015 | Wolf | G01C 5/06 702/166 |
| 2017/0089791 A1 * | 3/2017 | Tanabe | H04W 4/027 |

* cited by examiner

*Primary Examiner* — Hyun D Park
(74) *Attorney, Agent, or Firm* — MLO, a professional corp.

(57) ABSTRACT

Determining when a barometric-based approach for estimating an unknown altitude of a mobile device should not be used. Different approaches determine if estimating an unknown altitude of a mobile device using a measured atmospheric condition will result in an estimated altitude having acceptable or unacceptable error. If use of the measured atmospheric condition would result in acceptable error, the measured atmospheric condition is used to estimate the unknown altitude. If use of the measured atmospheric condition would result in unacceptable error, the measured atmospheric condition is not used to estimate the unknown altitude. The resultant altitude estimate is then used to locate the mobile device.

12 Claims, 6 Drawing Sheets

SYSTEMS AND METHODS FOR POSITIONING DURING ATYPICAL ATMOSPHERIC CONDITIONS

BACKGROUND

Determining the exact location of a mobile device, such as a cell phone or a locator, can be challenging, and imprecise estimates of the mobile device's altitude may have "life or death" consequences for the user, such as a user of a cell phone who has initiated a 911 call, or an emergency service provider, a rescue worker, a firefighter, a police officer, or other first responder who is wearing a locator.

Figure 1A:
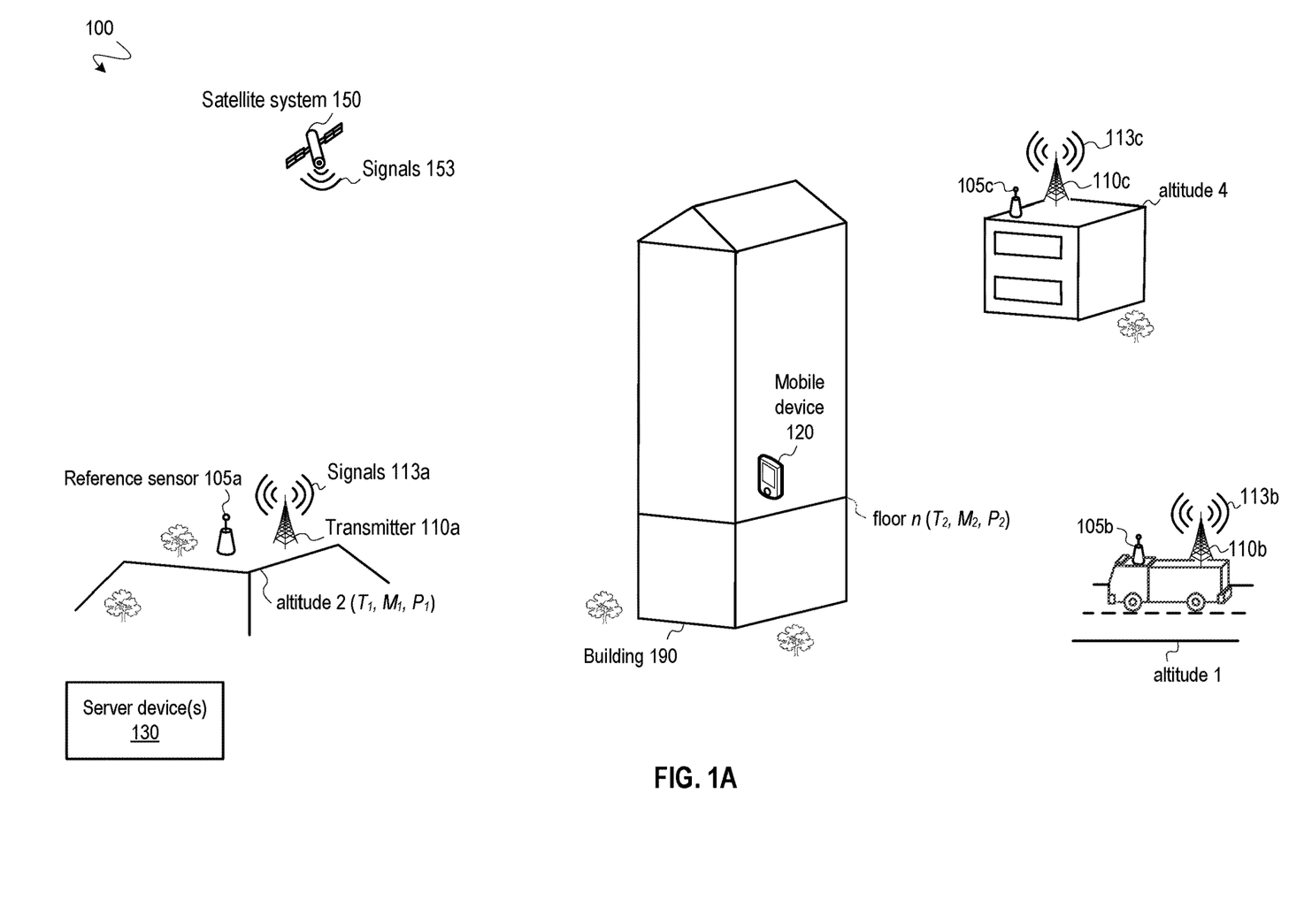
FIG. 1A depicts a system for estimating an unknown altitude of a mobile device.

One approach for estimating an unknown altitude of a mobile device uses the system 100 depicted in FIG. 1A, which includes one or more reference sensors 105 at respective known locations, one or more transmitters 110 at respective known locations, a mobile device 120 at an unknown altitude, one or more server devices 130, and satellite system 150 (e.g., a GNSS system).

Each of the reference sensors 105 may include one or more sensors for measuring atmospheric conditions such as pressure, temperature, humidity, gases in the air, or other conditions. The reference sensors 105 and the transmitters 110 are at known locations (e.g., in terms of latitude, longitude and altitude, or other coordinates), but need not reside at fixed locations. For example, any of the reference sensors 105 or the transmitters 110 may be mobile so long as their location at a given time of use is known. In one embodiment, a mobile reference sensor 105b and a mobile transmitter 110b are located on a first responder ground or aerial vehicle, and the position of that vehicle may be determined using known location technologies—e.g., performing trilateration, multilateration or another approach using ranging signals 113 from other transmitters 110 or ranging signals 153 from the satellite system 150.

The mobile device 120 may also include one or more sensors for measuring atmospheric conditions such as pressure, temperature, humidity, gases in the air, or other conditions.

The server devices 130 may include one or more location servers (e.g., E-SMLC, SLP, or other).

As known in the art, atmospheric conditions determined by devices of the system 100 may be used with the following barometric formula to estimate an unknown altitude of the mobile device 120, $h_{mobile}$, as follows:

$$h_{mobile} = h_{sensor} - \frac{RT}{gM}\ln\left(\frac{P_{sensor}}{P_{mobile}}\right), \quad \text{(Equation 1)}$$

where $P_{mobile}$ is an estimate of pressure at the location of the mobile device 120 that is usually a measurement of pressure from a pressure sensor of the mobile device 120, $P_{sensor}$ is an estimate of pressure at a location of a reference sensor from the reference sensors 105 that is usually a measurement of pressure from a pressure sensor of the reference sensor, T is an estimate of temperature at the unknown altitude that may be measured by a temperature sensor of the mobile device 120 or the reference sensor, $h_{sensor}$ is a known altitude of the reference sensor, g corresponds to the acceleration due to gravity, R is the universal gas constant, and M is an estimate of the molar mass of air at the unknown altitude that may be determined using a humidity sensor of the mobile device 120 or the reference sensor.

In some cases, the estimate of pressure at the location of the reference sensor, $P_{sensor}$, is converted to a reference pressure that specifies an estimate of pressure at a reference altitude as follows:

$$P_{ref} = P_{sensor}\exp\left(-\frac{gM(h_{ref} - h_{sensor})}{RT_{remote}}\right), \quad \text{(Equation 2)}$$

where $P_{ref}$ is the reference pressure, and $h_{ref}$ is the reference altitude. When a reference pressure is used, the attitude of the mobile device, $h_{mobile}$, is estimated using Equation 1, where $h_{ref}$ is substituted for $h_{sensor}$ and $P_{ref}$ is substituted for $P_{sensor}$. The reference altitude, $h_{ref}$ may be any altitude, and is often mean sea-level altitude. When two or more reference pressures are available, the reference pressures may be combined into a single reference pressure value using an average, weighted average, or other suitable combination of the reference pressures, and the single reference pressure value is used for the reference pressure, $P_{ref}$.

Using the barometric formula of Equation 1 to estimate altitude makes several assumptions. One assumption is that the temperature at the unknown altitude of the mobile device 120 is within a tolerated amount of temperature from the true temperature at that unknown altitude elsewhere in the system 100, including the lapse rate of temperature with height (degree/meter). Another assumption is that the molar mass of air at the unknown altitude of the mobile device 120 is within a tolerated amount of molar mass from the true molar mass of air at that unknown altitude elsewhere in the system 100. Yet another assumption is that the pressure at the unknown altitude of the mobile device 120 is within a tolerated amount of pressure from the true pressure at that unknown altitude elsewhere in the system 100. When these assumptions are true, the barometric formula of Equation 1 produces accurate estimates of altitude.

By way of example, FIG. 1A shows values of temperature $T_1$, molar mass $M_1$, and pressure $P_1$ at an altitude 2, and values of temperature $T_2$, molar mass $M_2$, and pressure $P_2$ at a floor n. When the altitude of floor n is equal to altitude 2, the values of temperature $T_1$, molar mass $M_1$, and/or pressure $P_1$ are respectively expected to be within tolerated amounts of the values of temperature $T_2$, molar mass $M_2$, and/or pressure $P_2$. Under most circumstances, any variance between the values is small enough (i.e., within a tolerated amount) to produce an estimated altitude that is within a maximum amount of error (e.g., three meters, which approximates one floor of a typical building) of true altitude, which is usually satisfactory. However, under the circumstances described below, the variance is large enough (i.e., not within a tolerated amount) to produce an estimated altitude that is not within the maximum amount of error from true altitude, which is usually unsatisfactory during emergency situations that have life or death consequences.

Figure 1B:
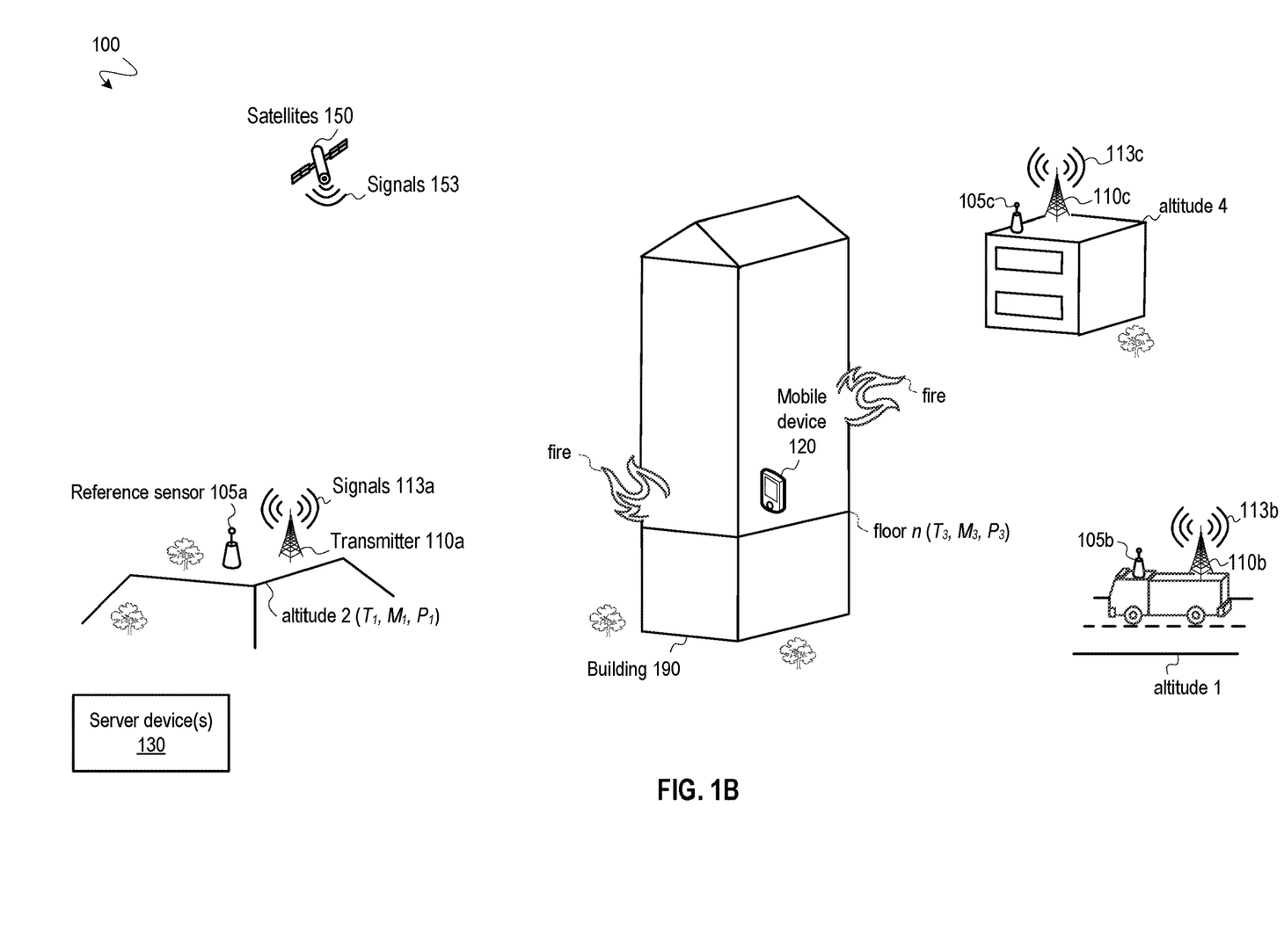
FIG. 1B depicts the system for estimating the unknown altitude of the mobile device when a volatile environmental condition is present.

The assumptions made when using the barometric formula of Equation 1 may not be made under certain circumstances, such as during a building fire that produces any of: different localized temperature (e.g., higher temperature) compared to the temperature experienced elsewhere in the system 100 for the same altitude; different localized molar mass of air (e.g., higher levels of $CO_2$ and/or water vapor) compared to the molar mass experienced elsewhere in the system 100 for the same altitude; and/or different localized pressure compared to the pressure experienced elsewhere in the system 100 for the same altitude. By way of example, FIG. 1B shows the values of temperature $T_1$, molar mass $M_1$, and pressure $P_1$ at an altitude 2, and values of temperature $T_3$, molar mass $M_3$, and pressure $P_3$ at the floor n when a fire is present at or near floor n. Under such conditions, the values of temperature $T_1$, molar mass $M_1$, and/or pressure $P_1$ are not expected to be within tolerated amounts of the values of temperature $T_3$, molar mass $M_3$, and/or pressure $P_3$, and the assumptions underlying Equation 1 will not hold true. As a consequence, any altitude estimate using Equation 1 is likely to differ from true altitude by more than the maximum amount of error, which often makes such estimated altitudes unusable during emergency situations.

Described below are approaches for determining when barometric-based approaches for estimating an unknown altitude of a mobile devices, like the approach illustrated by Equation 1, should not be used.

DETAILED DESCRIPTION

As discussed in the Background section, and with reference to FIG. 1A and FIG. 1B, an unknown altitude of the mobile device 120, $h_{mobile}$, can be estimated using the barometric formula of Equation 1 (reproduced below):

$$h_{mobile} = h_{sensor} - \frac{RT}{gM} \ln\left(\frac{P_{sensor}}{P_{mobile}}\right), \quad \text{(Equation 1)}$$

where $P_{mobile}$ is an estimate of pressure at the location of the mobile device 120, $P_{sensor}$ is an estimate of pressure at a location of a reference sensor from the reference sensors 105, T is an estimate of temperature at the unknown altitude that may be measured by a temperature sensor of the mobile device 120 or the reference sensor, $h_{sensor}$ is a known altitude of the reference sensor, g corresponds to the acceleration due to gravity, R is the universal gas constant, and M is an estimate of the molar mass of air at the unknown altitude that may be determined using a humidity sensor of the mobile device 120 or the reference sensor.

Use of the barometric formula of Equation 1 requires several assumptions.

Assumption about temperature: When the temperature T is not measured by a temperature sensor of the mobile device 120, and is instead measured by one of the reference sensors 105, it is assumed that the temperature at the unknown altitude of the mobile device 120 is within a tolerated amount of temperature from the temperature T. When the temperature T is measured by a temperature sensor of the mobile device 120, it is assumed that the temperature T reflects the temperature experienced elsewhere in the system at the unknown altitude, including the lapse rate of temperature with height (degree/meter).

Assumption about the molar mass of air: When the molar mass of air M is not determined based on measured air density at the location of the mobile device 120, and is instead determined based on measured air density at another location (e.g., a location of a reference sensor), it is assumed that the molar mass at the unknown altitude of the mobile device 120 is within a tolerated amount of the molar mass of air M. When the molar mass of air M is determined based on measured air density at the location of the mobile device 120, it is assumed that the molar mass of air M reflects the molar mass of air present elsewhere in the system at the unknown altitude.

Assumption about pressure: It is assumed that the estimate of pressure at the location of the mobile device 120, $P_{mobile}$, reflects the pressure experienced elsewhere in the system at the unknown altitude.

When the mobile device 120 experiences volatile atmospheric conditions, such as higher localized temperature, higher levels of $CO_2$ gas, or higher levels of evaporated water caused by a fire, the above assumptions cannot be made, and the barometric formula of Equation 1 is unlikely to produce an estimate of the unknown altitude of the mobile device 120 that is within a tolerated amount of error from the true altitude of the mobile device 120.

Given the low likelihood that the barometric formula of Equation 1 can be used to accurately estimate the unknown altitude of the mobile device 120 when the mobile device 120 is located in an environment with volatile atmospheric conditions, solutions are needed to detect those volatile atmospheric conditions so an alternative approach for estimating the unknown altitude of the mobile device 120 can be used, or so any estimates of the unknown altitude resulting from the barometric formula can be deprioritized or interpreted as being less accurate than when the mobile device 120 is not experiencing volatile atmospheric conditions. Such solutions are discussed below.

Figure 2:
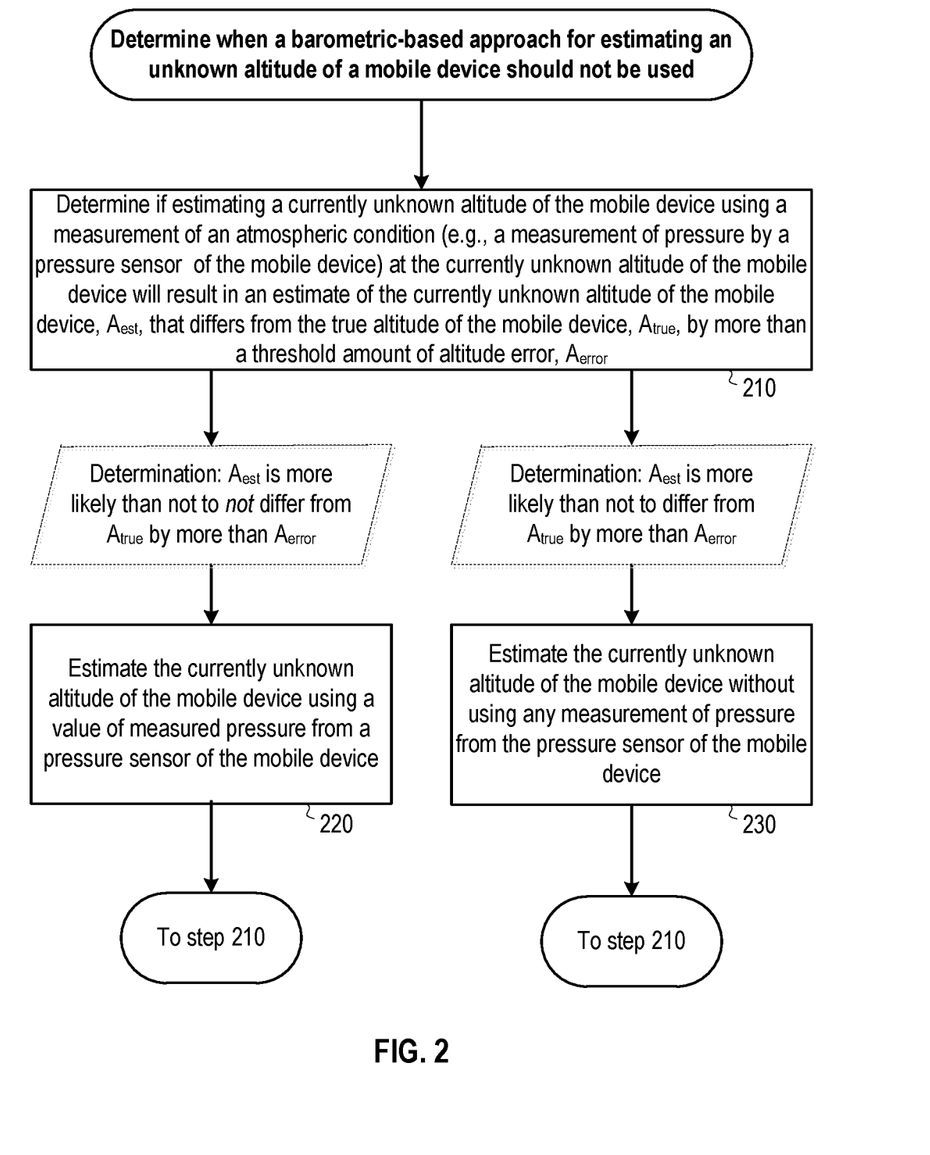
FIG. 2 provides a process for determining when a barometric-based approach for estimating an unknown altitude of a mobile device should not be used.

Determine when a Barometric-Based Approach for Estimating an Unknown Altitude of a Mobile Device should not be Used (FIG. 2)

As explained above, under volatile atmospheric conditions experienced by the mobile device 120, the barometric formula of Equation 1 should often not be used to estimate the unknown altitude of the mobile device 120.

FIG. 2 shows a process that selects an approach for estimating an unknown altitude of a mobile device depending on atmospheric conditions experienced by the mobile device. Such a process may determine when a barometric-based approach for estimating an unknown altitude of a mobile device should not be used. Benefits of the process of FIG. 2 include automatic detection of volatile atmospheric conditions so an appropriate approach for estimating an unknown altitude of a mobile device can be selected to optimally provide an estimate of the unknown altitude (e.g., preferably to within a tolerated amount of error from the true altitude of the mobile device).

As shown in FIG. 2, during step 210, a determination is made as to whether estimating a currently unknown altitude of the mobile device using a measurement of an atmospheric condition at the currently unknown altitude of the mobile device (e.g., using a measurement of pressure by a pressure sensor of the mobile device and/or a measurement of temperature by a temperature sensor of the mobile device) will result in an estimate of the currently unknown altitude of the mobile device, $A_{est}$, that differs from the true altitude of the mobile device, $A_{true}$, by more than a threshold amount of altitude error, $A_{error}$. By way of example, an estimate of the currently unknown altitude of the mobile device, $A_{est}$, that could differ from the true altitude of the mobile device, $A_{true}$, by more than the threshold amount of altitude error, $A_{error}$, could be lower or higher than the true altitude of the mobile device, $A_{true}$, depending on the measurement of the atmospheric condition at the currently unknown altitude of the mobile device. By way of example, different implementations of step 210 are discussed below with reference to FIG. 3 and FIG. 4.

If, during step 210, it is determined that the estimate of the currently unknown altitude of the mobile device, $A_{est}$, is more likely than not to be within the threshold amount of altitude error, $A_{error}$, from the true altitude of the mobile device, $A_{true}$, (i.e., is more likely than not to not differ from the true altitude of the mobile device, $A_{true}$, by more than the threshold amount of altitude error, $A_{error}$), then, during step 220, the currently unknown altitude is estimated using the measurement of the atmospheric condition (e.g., using the barometric formula of Equation 1 or another suitable equation, along with the measurement of pressure by the pressure sensor of the mobile device, and/or along with the measurement of temperature from the temperature sensor of the mobile device if the measurement of temperature is used). After step 220, the process repeats for new unknown altitudes of the mobile device.

If, during step 210, it is determined that the estimate of the currently unknown altitude of the mobile device, $A_{est}$, is more likely than not to not be within the threshold amount of altitude error, $A_{error}$, from the true altitude of the mobile device, $A_{true}$ (i.e., is more likely than not to differ from the true altitude of the mobile device, $A_{true}$, by more than the threshold amount of altitude error, $A_{error}$), then, during step 230, the currently unknown altitude is estimated without using the measurement of the atmospheric condition (e.g., without using the measurement of pressure from the pressure sensor of the mobile device and/or the measurement of temperature from the temperature sensor of the mobile device with the barometric formula of Equation 1 or another suitable equation), or without using any measurement of the atmospheric condition, including the measurement of the atmospheric condition. After step 230, the process repeats for new unknown altitudes of the mobile device.

Examples of step 230 include: (i) adjusting a previously-determined estimate of a previously unknown altitude of the mobile device using an estimate of movement by the mobile device between the previously unknown altitude and the currently unknown altitude; (ii) performing trilateration, multilateration, or another approach using estimated ranges determined by the estimated travel time of terrestrial or satellite ranging signals that were received by the mobile device at the currently unknown altitude; or (iii) using another approach. By way of example, the estimate of movement during option (i) is determined using one or more inertial sensors of the mobile device that track movement of the mobile device over time in up to three spatial dimensions, where such tracking is known in the art.

An alternative embodiment of step 230 includes estimating the currently unknown altitude using the barometric formula of Equation 1 and a measurement of pressure from the mobile device, and generating a confidence value indicating that the resulting estimate of the currently unknown altitude, $A_{est}$, is more likely than not to differ from the true altitude of the mobile device, $A_{true}$, by more than the threshold amount of altitude error, $A_{error}$.

As mentioned previously, different implementations of step 210 are provided in FIG. 3 and FIG. 4, which are discussed in the following section.

Determining if Estimating an Unknown Altitude of the Mobile Device Using a Measurement of an Atmospheric Condition at the Location of the Mobile Device Will Result in an Unacceptable Error (Step 210)

Figure 3:
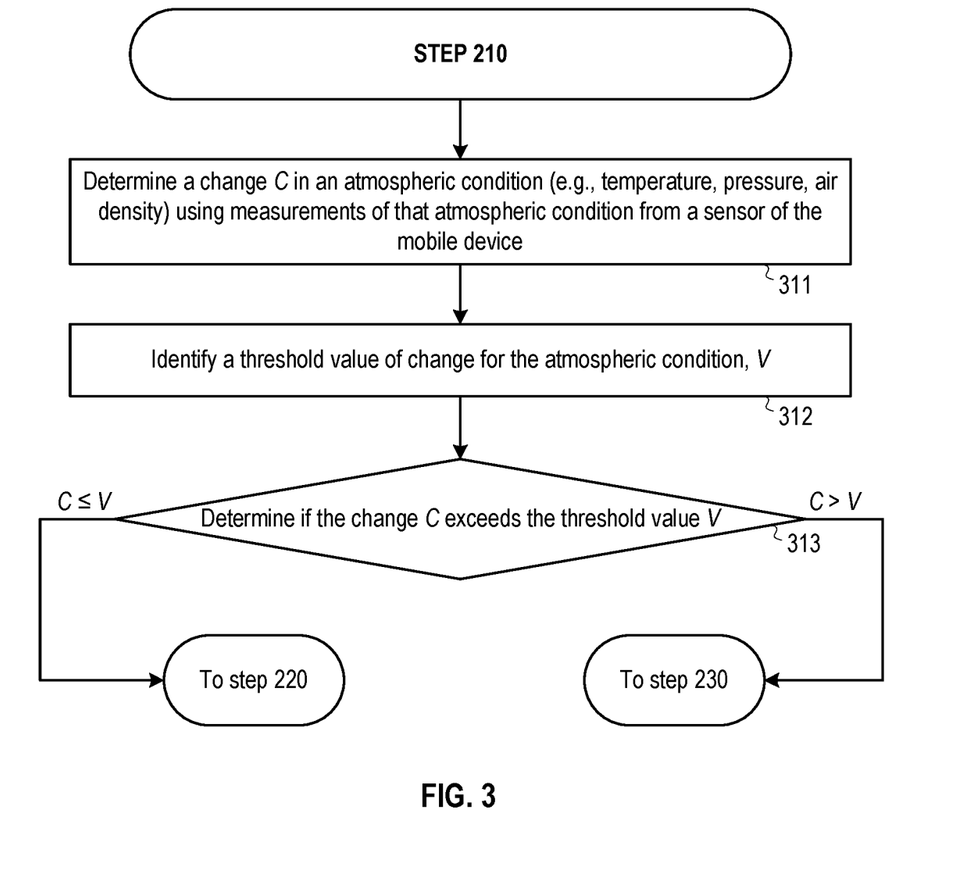
FIG. 3 provides a process for determining if estimating an unknown altitude of the mobile device using a measurement of an atmospheric condition at the unknown altitude of the mobile device will result in an estimate of the unknown altitude that differs from the true altitude of the mobile device by more than a threshold amount of altitude error.

FIG. 3 shows a first implementation of step 210, during which a determination is made if estimating a currently unknown altitude of the mobile device using a measurement of an atmospheric condition at the location of the mobile device will result in an estimate of the currently unknown altitude, $A_{est}$, that differs from the true altitude of the mobile device, $A_{true}$, by more than a threshold amount of altitude error, $A_{error}$. As shown, during step 311, a change C in an atmospheric condition is determined using measurements of that atmospheric condition from a suitable sensor of the mobile device. By way of example, the atmospheric condition may be any of temperature, pressure, and/or air density, which are respectively measured by a temperature sensor, a pressure sensor, and/or a humidity or gas sensor. During step 312, a threshold value of change, V, for the atmospheric condition is identified. By way of example, the identification may be made by looking up the threshold value V from a memory source (e.g., a table in a database). During step 313, a determination is made as to whether the change C exceeds the threshold value V. If, during step 313, it is determined that the change C does not exceed the threshold value V (i.e., C≤V), then the process proceeds to step 220 of FIG. 2. If, during step 313, it is determined that the change C exceeds the threshold value V (i.e., C>V), then the process proceeds to step 230 of FIG. 2.

In one embodiment of FIG. 3, the change C relates to a difference d between two measurements separated by a time period t—i.e., C=d/t. By way of example, when the atmospheric condition is temperature, the difference d may be +50 degrees (where degrees are in Fahrenheit, Celsius, Kelvin, or other) or another number, the time period t may be 5 seconds or another number, and the threshold value V of change may be 4 degrees per second or another number. By way of example, when the atmospheric condition is pressure, the difference d may be +/−20 pascals (Pa) or another number, the time period t may be less than 10 seconds or another number, and the threshold value V of change may be 2 Pa per second.

In some embodiments, the monitored threshold value V may require a change C in one direction where the threshold value V is positive or negative. Such values are useful to determine if the change C indicates that measured conditions are rising or falling, which may indicate that the mobile device is entering or leaving extreme conditions. By way of example, a large increase in temperature over a short time period (e.g., +50 degrees over 5 seconds) may indicate that a fire fighter with a mobile device is going into a burning building such that calculated altitude estimates based on pressure measured by the mobile device and the barometric formula may be erroneous. A large decrease in temperature over a short time period (e.g., −50 degrees over 5 seconds) may indicate a fire fighter with a mobile device is leaving a burning building such that calculated altitude estimates based on pressure measured by the mobile device and the barometric formula may be used.

In some embodiments, changes of multiple conditions over time may be compared to threshold values. For example, a change in temperature exceeding a first threshold value and a change in pressure exceeding a second threshold value may collectively indicate the calculated altitude estimates based on pressure measured by the mobile device and the barometric formula may be erroneous.

Figure 4:
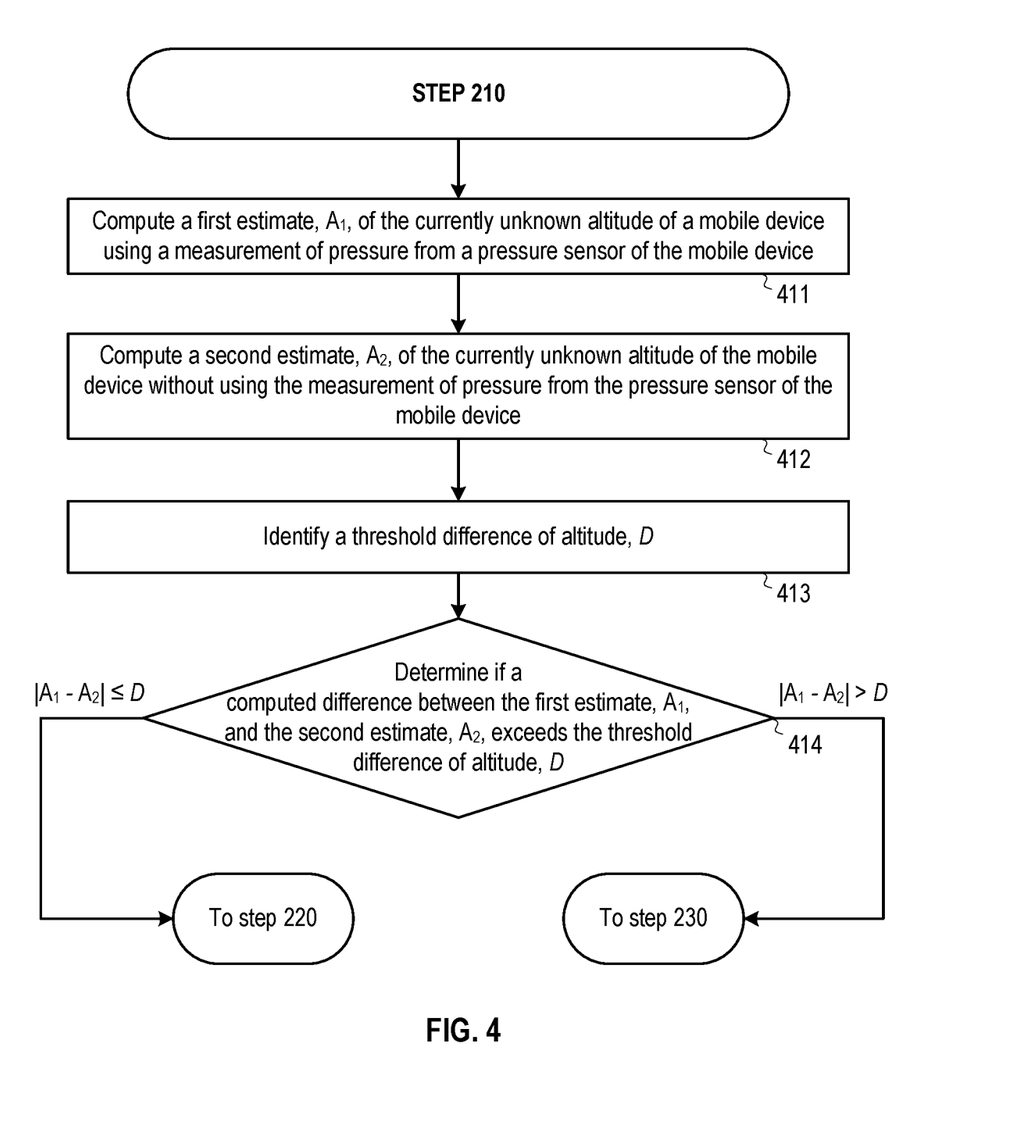
FIG. 4 provides another process for determining if estimating an unknown altitude of the mobile device using a measurement of an atmospheric condition at the unknown altitude of the mobile device will result in an estimate of the unknown altitude that differs from the true altitude of the mobile device by more than a threshold amount of altitude error.

FIG. 4 shows a second implementation of step 210, during which a determination is made if estimating a currently unknown altitude of the mobile device using a measurement of an atmospheric condition at the location of the mobile device will result in an estimate of the currently unknown altitude, $A_{est}$, that differs from the true altitude of the mobile device, $A_{true}$, by more than a threshold amount of altitude error, $A_{error}$. As shown, during step 411, a first estimate, $A_1$, of the currently unknown altitude of the mobile device is computed using a measurement of pressure from a pressure sensor of the mobile device. By way of example, computation may occur using the barometric formula of Equation 1 or another suitable equation. During step 412, a second estimate, $A_2$, of the currently unknown altitude is computed without using the measurement of pressure from the pressure sensor of the mobile device. During step 413, a threshold difference D of altitude is identified. By way of example, the identification may be made by looking up the threshold difference D from a memory source (e.g., a table in a database). During step 414, a determination is made as to whether a computed difference between the first estimate, $A_1$, and the second estimate, $A_2$, exceeds the threshold difference of altitude, D. If, during step 414, it is determined that the computed difference does not exceed the threshold difference D (i.e., $|A_1-A_2| \leq D$), then the process proceeds to step 220 of FIG. 2. If, during step 414, it is determined that the computed difference exceeds the threshold difference D (i.e., $|A_1-A_2| > D$), then the process proceeds to step 230 of FIG. 2.

Examples of step 412 include: (i) adjusting a previously-determined estimate of a previously unknown altitude of the mobile device using an estimate of movement by the mobile device between the previously unknown altitude and the currently unknown altitude; (ii) performing trilateration, multilateration, or another approach using estimated ranges determined by the estimated travel time of terrestrial or satellite ranging signals that were received by the mobile device at the currently unknown altitude; or (iii) using another approach. By way of example, the estimate of movement during option (i) is determined using one or more inertial sensors of the mobile device that track movement of the mobile device over time in up to three spatial dimensions, where such tracking is known in the art.

In a third implementation of step 210, a gas-measuring sensor (e.g., of the mobile device; e.g., separate from the mobile device, but co-located with or in the same building as the mobile device) measures a localized amount of CO2 or other gas in the air. A tolerated threshold amount of gas is identified (e.g., a maximum amount of that gas that is expected to be airborne) and compared to the measured amount of gas from the gas-measuring sensor. If the measured amount of gas does not exceed the tolerated threshold amount of gas, then the process proceeds to step 220 of FIG. 2. If the measured amount of gas exceeds the tolerated threshold amount of gas, then the process proceeds to step 230 of FIG. 2.

Additional aspects describing particular implementations of the processes shown in FIG. 2, FIG. 3, and FIG. 4 are described below.

Other Aspects

Examples of localized, volatile atmospheric conditions described above have focused on volatile conditions caused by fires. Other situations that produce localized, volatile atmospheric conditions are also contemplated, including conditions caused by water (e.g., during drowning rescues), chemical attacks, releases of gas into the air, and other situations that would be readily understood by one of ordinary skill in the art.

The term altitude used herein may refer to an altitude, an elevation, height, height above a reference ellipsoid, or another measurement. An altitude may be associated with a particular floor that can be looked up using the altitude.

Figure 5:
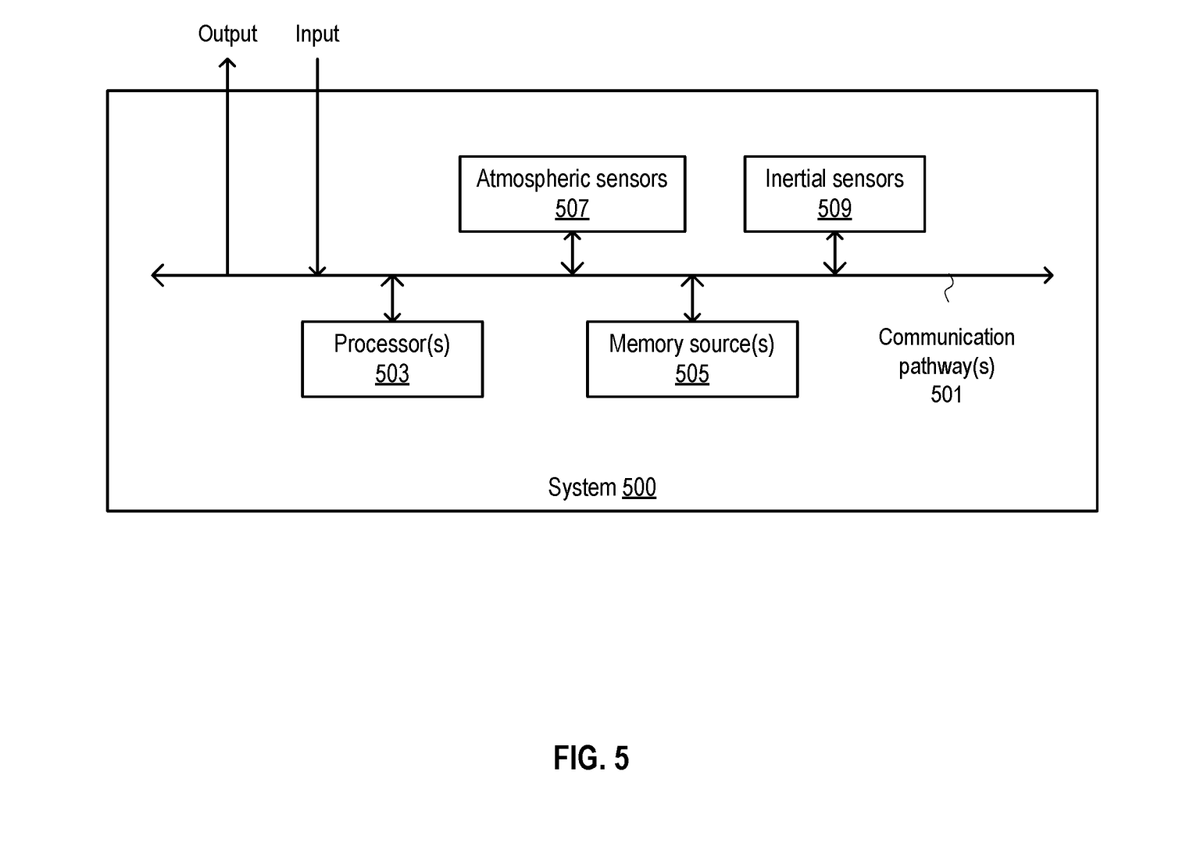
FIG. 5 depicts a system for use in performing operations described herein, including operations of determination, estimation, computation, identification and others described in relation to other figures.

By way of example, FIG. 5 depicts components of a system 500 for use in performing operations described herein, including determination, estimation, computation, and identification operations of FIG. 2, FIG. 3 and FIG. 4. In different embodiments, some of all of the components of the system 500 reside in the mobile device 120, one of the server devices 130, or another device, or are distributed throughout a network across different devices. As shown in FIG. 5, the system 500 includes one or more communication pathways 201 that interconnect various components together as would be known in the art, including both wireless and wired pathways. In one embodiment, the pathways 501 include one or more buses connected to each other through various bridges, controllers and/or adapters as is well known in the art. One or more processors 503 are coupled to one or more memory sources 505 using the pathway(s) 501. The one or more memory sources 505 may include one or more non-transitory processor-readable media embodying program instructions that, when executed by the one or more processors 503, cause the one or more processors 503 to perform or implement operations disclosed herein, including any or all steps of FIG. 2, FIG. 3 and/or FIG. 4. Steps of determining, estimating, computing, and identifying may be performed by the processor(s) 503 or another suitable machine. Information resulting from each determination, estimation, computation or other step may be stored in the memory source(s) 505. The one or more memory sources 505 may also include storage for data that is used in FIG. 2, FIG. 3, and/or FIG. 4, including such data as the threshold amount of altitude error of FIG. 2, the threshold value of change for the atmospheric condition of FIG. 3, the threshold difference of altitude of FIG. 4, and the values of g, R, M, $h_{ref}$, and/or $h_{sensor}$ used in the barometric formula of Equation 1. Well-known approaches for exchanging data between the memory source(s) 505 and other components like the processor(s) 503 may be used to carry out the processes of FIG. 2, FIG. 3, and FIG. 4. The system 500 also includes atmospheric sensors 507 that measure atmospheric conditions (e.g., pressure, temperature, humidity, other), and inertial sensors 509 that measure motion (e.g., distances traveled along particular directions, at particular speeds), where measurements of these sensors are made using known techniques. By way of example, when the system 500 is the mobile device 120, the atmospheric sensors 507 provide the estimate of pressure at the unknown altitude ($P_{mobile}$), and optionally provide the estimate of the temperature at the unknown altitude (7).

The system 500 is also shown to receive input and to provide output, which may be facilitated using known components for receiving input and providing output. When the system 500 is the mobile device 120, the input may include: the reference pressure ($P_{ref}$) or the measurement pressure from the reference sensor ($P_{sensor}$), the reference altitude ($h_{ref}$) or the altitude of the reference sensor ($h_{sensor}$), a temperature from a reference sensor (7), the molar mass (M), and other variables needed to perform particular implementations of the barometric formula of Equation 1; the threshold amount of altitude error of FIG. 2, the threshold value of change for the atmospheric condition of FIG. 3, the threshold difference of altitude of FIG. 4; and/or ranging signals from the transmitters 110 or the satellite system 150 for use in determining pseudoranges that are used during trilateration processing if such processing is desired. When the system 500 is one of the server devices 130, the input may include the same input as listed above for the mobile device 120 in addition to the estimate of pressure at the unknown altitude ($P_{mobile}$), and a temperature from the mobile device (T) if used when performing particular implementations of the barometric formula of Equation 1. The input may further include pseudoranges that were determined based on ranging signals received by the mobile device 120.

Methods of this disclosure may be implemented by hardware, firmware or software. One or more non-transitory machine-readable media embodying program instructions that, when executed by one or more machines, cause the one or more machines to perform or implement operations comprising the steps of any of the methods described herein are contemplated. As used herein, machine-readable media includes all forms of machine-readable media (e.g. non-volatile or volatile storage media, removable or non-removable media, integrated circuit media, magnetic storage media, optical storage media, or any other storage media) that may be patented under the laws of the jurisdiction in which this application is filed, but does not include machine-readable media that cannot be patented under the laws of the jurisdiction in which this application is filed.

By way of example, machines may include one or more computing device(s), processor(s), controller(s), integrated circuit(s), chip(s), system(s) on a chip, server(s), programmable logic device(s), other circuitry, and/or other suitable means described herein or otherwise known in the art. Systems that include one or more machines or the one or more non-transitory machine-readable media embodying program instructions that, when executed by the one or more machines, cause the one or more machines to perform or implement operations comprising the steps of any methods described herein are also contemplated.

Method steps described herein may be order independent, and can therefore be performed in an order different from that described. It is also noted that different method steps described herein can be combined to form any number of methods, as would be understood by one of skill in the art. It is further noted that any two or more steps described herein may be performed at the same time. Any method step or feature disclosed herein may be expressly restricted from a claim for various reasons like achieving reduced manufacturing costs, lower power consumption, and increased processing efficiency. Method steps performed by a transmitter or a mobile device can be performed by a server, or vice versa.

Systems comprising one or more modules that perform, are operable to perform, or adapted to perform different method steps/stages disclosed herein are also contemplated, where the modules are implemented using one or more machines listed herein or other suitable hardware. When two things (e.g., modules or other features) are "coupled to" each other, those two things may be directly connected together, or separated by one or more intervening things. Where no lines and intervening things connect two particular things, coupling of those things is contemplated in at least one embodiment unless otherwise stated. Where an output of one thing and an input of another thing are coupled to each other, information sent from the output is received by the input even if the data passes through one or more intermediate things. Different communication pathways and protocols may be used to transmit information disclosed herein. Information like data, instructions, commands, signals, bits, symbols, and chips and the like may be represented by voltages, currents, electromagnetic waves, magnetic fields or particles, or optical fields or particles.

The words comprise, comprising, include, including and the like are to be construed in an inclusive sense (i.e., not limited to) as opposed to an exclusive sense (i.e., consisting only of). Words using the singular or plural number also include the plural or singular number, respectively. The word or and the word and, as used in the Detailed Description, cover any of the items and all of the items in a list. The words some, any and at least one refer to one or more. The term may is used herein to indicate an example, not a requirement—e.g., a thing that may perform an operation or may have a characteristic need not perform that operation or have that characteristic in each embodiment, but that thing performs that operation or has that characteristic in at least one embodiment.

A mobile device may include any of: antenna(s) for exchanging signals with other systems; RF front end module(s) with circuitry components that are known in the art; processing module(s) for signal processing of received signals to determine position information (e.g., times of arrival or travel time of ranging signals, atmospheric information from transmitters, and/or location or other information associated with each transmitter or satellite); processing module(s) for using the position information to compute an estimated position of the mobile device (e.g., computing estimates of distances between the mobile device and different transmitters or satellites, and then using those estimates of distances along with known locations of the transmitters or satellites during the well-known process of trilateration to compute the estimated position in up to three dimensions); interface module(s) for exchanging information with other systems via other links other than a radio link; and/or I/O module(s) for permitting user interaction with the mobile device.

Related Applications

This application relates to the following related application(s): U.S. Pat. Appl. No. 62/540,549, filed 2017 Aug. 2, entitled SYSTEMS AND METHODS FOR POSITIONING DURING ATYPICAL ATMOSPHERIC CONDITIONS. The content of each of the related application(s) is hereby incorporated by reference herein in its entirety.

The invention claimed is:

1. A method for determining an estimate of a currently unknown altitude of a mobile device, wherein the method comprises:

receiving, by the mobile device, signals indicative of location information, determining a location of the mobile device using the location information, measuring an atmospheric condition at the location of the mobile device using a temperature sensor, a pressure sensor, a humidity sensor, or a gas sensor of the mobile device, identifying a threshold value of change for the measured atmospheric condition, automatically detecting occurrences of the measured atmospheric condition including a non-volatile atmospheric condition that does not exceed the threshold value of change and a volatile atmospheric condition that exceeds the threshold value of change, in response to the non-volatile atmospheric condition, determining the estimate of the currently unknown altitude of the mobile device using the measured atmospheric condition as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured atmospheric condition, wherein the measured atmospheric condition is temperature, pressure or air density.

2. The method of claim 1, wherein:

the estimate of movement by the mobile device is between a previously-determined estimate of a previously unknown altitude and the currently unknown altitude.

3. A method for determining an estimate of a currently unknown altitude of a mobile device, wherein the method comprises:

receiving, by the mobile device, signals indicative of location information, determining a location of the mobile device using the location information, measuring an atmospheric condition at the location of the mobile device using a temperature sensor, a pressure sensor, a humidity sensor, or a gas sensor of the mobile device, computing a first estimate of the currently unknown altitude of the mobile device using the measured atmospheric condition, computing a second estimate of the currently unknown altitude of the mobile device without using the measured atmospheric condition, identifying a threshold difference of altitude, automatically detecting occurrences of the measured atmospheric condition including a non-volatile atmospheric condition for which a computed difference between the first estimate and the second estimate does not exceed the threshold difference of altitude and a volatile atmospheric condition for which the computed difference between the first estimate and the second estimate exceeds the threshold difference of altitude, in response to the non-volatile atmospheric condition, determining the estimate of the currently unknown altitude of the mobile device using the measured atmospheric condition as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signal received by the mobile device from transmitters at known locations or a satellite system and without using the measured atmospheric condition, wherein the measured atmospheric condition is temperature, pressure or air density; and wherein the second estimate is computed by using a previously-determined estimate of a previously unknown altitude of the mobile device and an estimate of movement by the mobile device between the previously unknown altitude and the currently unknown altitude.

4. A method for determining an estimate of a currently unknown altitude of a mobile device wherein the method comprises:

receiving, by the mobile device, signals indicative of location information, determining a location of the mobile device using the location information, measuring a pressure value at the location of the mobile device using a pressure sensor of the mobile device, measuring a localized amount of CO2 or other gas in the air at the location of the mobile device using a gas-measuring sensor co-located with the mobile device, identifying a tolerated threshold amount of gas, automatically detecting occurrences of the measured atmospheric condition including a non-volatile atmospheric condition for which the measured amount of gas does not exceed the tolerated threshold amount of gas and a volatile atmospheric condition for which the measured amount of gas exceeds the tolerated threshold amount of gas, in response to the non-volatile atmospheric condition, determining the estimate of the currently unknown altitude of the mobile device using the measured pressure value from the pressure sensor of the mobile device as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured pressure value from the pressure sensor of the mobile device;

wherein determining the estimate of the currently unknown altitude of the mobile device without using the measured pressure value comprises:

estimating the currently unknown altitude of the mobile device using a previously-determined estimate of a previously unknown altitude of the mobile device and the estimate of movement by the mobile device between the previously unknown altitude and the currently unknown altitude.

5. One or more non-transitory processor-readable media embodying program instructions that, when executed by one or more processors, cause the one or more processors to implement a method for determining an estimate of a currently unknown altitude of a mobile device, wherein the method comprises:

receiving, by the mobile device, signals indicative of location information, determining a location of the mobile device using the location information, measuring an atmospheric condition at the location of the mobile device using a temperature sensor, a pressure sensor, a humidity sensor, or a gas sensor of the mobile device, identifying a threshold value of change for the measured atmospheric condition, automatically detecting occurrences of the measured atmospheric condition including a non-volatile atmospheric condition that does not exceed the threshold value of change and a volatile atmospheric condition that exceeds the threshold value of change, in response to the non-volatile atmospheric condition, determining the estimate of the currently unknown altitude of the mobile device using the measured atmospheric condition as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured atmospheric condition, wherein the measured atmospheric condition is temperature, pressure or air density.

6. The one or more non-transitory processor-readable media of claim 5, wherein:

the estimate of movement by the mobile device is between a previously-determined estimate of a previously unknown altitude and the currently unknown altitude.

7. One or more non-transitory processor-readable media embodying program instructions that, when executed by one or more processors, cause the one or more processors to implement a method for determining an estimate of a currently unknown altitude of a mobile device, wherein the method comprises:

receiving, by the mobile device, signals indicative of location information, determining a location of the mobile device using the location information, measuring an atmospheric condition at the location of the mobile device using a temperature sensor, a pressure sensor, a humidity sensor, or a gas sensor of the mobile device, computing a first estimate of the currently unknown altitude of the mobile device using the measured atmospheric condition, computing a second estimate of the currently unknown altitude of the mobile device without using the measured atmospheric condition, identifying a threshold difference of altitude, automatically detecting occurrences of the measured atmospheric condition including a non-volatile atmospheric condition for which a computed difference between the first estimate and the second estimate does not exceed the threshold difference of altitude and a volatile atmospheric condition for which the computed difference between the first estimate and the second estimate exceeds the threshold difference of altitude, in response to the non-volatile atmospheric condition, determining the estimate of the currently unknown altitude of the mobile device using the measured atmospheric condition as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured atmospheric condition, wherein the measured atmospheric condition is temperature, pressure or air density; and wherein the second estimate is computed by using a previously-determined estimate of a previously unknown altitude of the mobile device and an estimate of movement by the mobile device between the previously unknown altitude and the currently unknown altitude.

8. One or more non-transitory processor-readable media embodying program instructions that, when executed by one or more processors, cause the one or more processors to implement a method for determining an estimate of a currently unknown altitude of a mobile device, wherein the method comprises:

receiving, by the mobile device, signals indicative of location information, determining a location of the mobile device using the location information, measuring a pressure value at the location of the mobile device using a pressure sensor of the mobile device, measuring a localized amount of CO2 or other gas in the air at the location of the mobile device using a gas-measuring sensor co-located with the mobile device, identifying a tolerated threshold amount of gas, automatically detecting occurrences of the measured atmospheric condition including a non-volatile atmospheric condition for which the measured amount of gas does not exceed the tolerated threshold amount of gas and a volatile atmospheric condition for which the measured amount of gas exceeds the tolerated threshold amount of gas, in response to the non-volatile atmospheric condition, determining the estimate of the currently unknown altitude of the mobile device using the measured pressure value from the pressure sensor of the mobile device as an input to a known barometric formula that is used to estimate altitude of the mobile device, and in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured pressure value from the pressure sensor of the mobile device;

wherein determining the estimate of the currently unknown altitude of the mobile device without using the measured pressure value comprises:

estimating the currently unknown altitude of the mobile device using a previously-determined estimate of a previously unknown altitude of the mobile device and the estimate of movement by the mobile device between the previously unknown altitude and the currently unknown altitude.

9. A system comprising a memory storing executable instructions and a processor coupled to the memory, wherein the processor performs a method for determining an estimate of a currently unknown altitude of a mobile device by executing the instructions stored in the memory, and wherein the method comprises:
   receiving, by the mobile device, signals indicative of location information,
   determining a location of the mobile device using the location information,
   measuring an atmospheric condition at the location of the mobile device using a temperature sensor, a pressure sensor, a humidity sensor, or a gas sensor of the mobile device,
   identifying a threshold value of change for the measured atmospheric condition,
   automatically detecting occurrences of the measured atmospheric condition including a non-volatile atmospheric condition that does not exceed the threshold value of change and a volatile atmospheric condition that exceeds the threshold value of change,
   in response to the non-volatile atmospheric condition, determining the estimate of the currently unknown altitude of the mobile device using the measured atmospheric condition as an input to a known barometric formula that is used to estimate altitude of the mobile device, and
   in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured atmospheric condition,
   wherein the measured atmospheric condition is temperature, pressure or air density.

10. The system of claim 9, wherein:
   the estimate of movement by the mobile device is between a previously-determined estimate of a previously unknown altitude and the currently unknown altitude.

11. A system comprising a memory storing executable instructions and a processor coupled to the memory, wherein the processor performs a method for determining an estimate of a currently unknown altitude of a mobile device by executing the instructions stored in the memory, and wherein the method comprises:
   receiving, by the mobile device, signals indicative of location information,
   determining a location of the mobile device using the location information,
   measuring an atmospheric condition at the location of the mobile device using a temperature sensor, a pressure sensor, a humidity sensor, or a gas sensor of the mobile device,
   computing a first estimate of the currently unknown altitude of the mobile device using the measured atmospheric condition,
   computing a second estimate of the currently unknown altitude of the mobile device without using the measured atmospheric condition,
   identifying a threshold difference of altitude,
   automatically detecting occurrences of the measured atmospheric condition including a non-volatile atmospheric condition for which a computed difference between the first estimate and the second estimate does not exceed the threshold difference of altitude and a volatile atmospheric condition for which the computed difference between the first estimate and the second estimate exceeds the threshold difference of altitude,
   in response to the non-volatile atmospheric condition, determining the estimate of the currently unknown altitude of the mobile device using the measured atmospheric condition as an input to a known barometric formula that is used to estimate altitude of the mobile device, and
   in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured atmospheric condition,
   wherein the measured atmospheric condition is temperature, pressure or air density; and
   wherein the second estimate is computed by using a previously-determined estimate of a previously unknown altitude of the mobile device and an estimate of movement by the mobile device between the previously unknown altitude and the currently unknown altitude.

12. A system comprising a memory storing executable instructions and a processor coupled to the memory, wherein the processor performs a method for determining an estimate of a currently unknown altitude of a mobile device by executing the instructions stored in the memory, and wherein the method comprises:
   receiving, by the mobile device, signals indicative of location information,
   determining a location of the mobile device using the location information,
   measuring a pressure value at the location of the mobile device using a pressure sensor of the mobile device,
   measuring a localized amount of $CO_2$ or other gas in the air at the location of the mobile device using a gas-measuring sensor co-located with the mobile device,
   identifying a tolerated threshold amount of gas,
   automatically detecting occurrences of the measured atmospheric condition including a non-volatile atmospheric condition for which the measured amount of gas does not exceed the tolerated threshold amount of gas and a volatile atmospheric condition for which the measured amount of gas exceeds the tolerated threshold amount of gas,
   in response to the non-volatile atmospheric condition, determining the estimate of the currently unknown altitude of the mobile device using the measured pressure value from the pressure sensor of the mobile device as an input to a known barometric formula that is used to estimate altitude of the mobile device, and
   in response to the volatile atmospheric condition, determining the estimate of the currently unknown altitude of the mobile device using an estimate of movement by the mobile device determined using an inertial sensor of the mobile device or using terrestrial or satellite ranging signals received by the mobile device from transmitters at known locations or a satellite system and without using the measured pressure value from the pressure sensor of the mobile device;

wherein determining the estimate of the currently unknown altitude of the mobile device without using the measured pressure value comprises:

estimating the currently unknown altitude of the mobile device using a previously-determined estimate of a previously unknown altitude of the mobile device and the estimate of movement by the mobile device between the previously unknown altitude and the currently unknown altitude.

* * * * *